United States Patent [19]

Ruschke

[11] Patent Number: 4,548,600

[45] Date of Patent: Oct. 22, 1985

[54] DRIP CHAMBER ASSEMBLY

[75] Inventor: Ricky R. Ruschke, McHenry, Ill.

[73] Assignee: Baxter Travenol Laboratories, Inc., Deerfield, Ill.

[21] Appl. No.: 131,265

[22] Filed: Mar. 17, 1980

[51] Int. Cl.⁴ ............................................. A61M 5/16
[52] U.S. Cl. ..................................... 604/122; 604/251
[58] Field of Search ........... 128/214 C, 214 R, 214 F, 128/214.2, 231; 604/122, 251

[56] References Cited

U.S. PATENT DOCUMENTS

| | | | |
|---|---|---|---|
| 2,837,091 | 6/1958 | McMinn | 128/214 |
| 3,465,784 | 9/1969 | Cofoid | 128/214 |
| 3,478,184 | 11/1969 | Cofoid | 128/214 |
| 3,970,084 | 7/1976 | Raines | 128/214 C |
| 4,037,597 | 7/1977 | Forberg | 128/214 |
| 4,038,983 | 8/1977 | Mittleman | 128/214 C |
| 4,173,223 | 11/1979 | Raines | 128/214 C |
| 4,175,558 | 11/1979 | Hess | 128/214 C |
| 4,222,407 | 9/1980 | Ruschke et al. | 137/855 |

*Primary Examiner*—Richard J. Johnson
*Attorney, Agent, or Firm*—John P. Kirby, Jr.; George H. Gerstman

[57] ABSTRACT

A drip chamber assembly is provided which includes a chamber that is flexible but is non-collapsible under a negative pressure condition. The chamber, being flexible, yields to priming easily, but when restriction is added to the inlet port the chamber will not collapse and aspirate air to the patient. A flexible chamber is formed of a vinyl plastic material having a thickness of about 0.04 inch to 0.08 inch and a durometer reading of about 61 shore A to 81 shore A. End caps rigidly support each of the ends of the chamber with the end caps each having a contact length along the chamber of at least 0.2 inch.

6 Claims, 3 Drawing Figures

DRIP CHAMBER ASSEMBLY

BACKGROUND OF THE INVENTION

The present invention concerns a novel drip chamber and, more particularly, a drip chamber that is suitable for use in medical administration sets.

Drip chambers are widely used in the administration of liquids to patients. Often the drip chamber is connected at the outlet of a burette or the drip chamber may be connected to the outlet of a container (i.e., bottle or bag) containing parenteral liquid, blood, or any other liquid that is intended to be administered to the patient. Typically the drip chamber assembly includes an inlet connected to a drop former, and a plastic chamber, with the inlet communicating with the inside of the plastic chamber via the drop former. In order to commence the flow of liquid to the patient, the drip chamber is conventionally primed by squeezing the chamber with the first two fingers and the thumb.

It is very desirable that the drip chamber have the ability to be primed easily. To this end, the drip chamber must be sufficiently flexible to enable the operator to prime the chamber easily by squeezing the chamber with the operator's first two fingers and thumb so that a sufficient amount of air can be displaced and liquids can flow into the drip chamber. It would appear that in order to make priming easier, a drip chamber having a thinner or more flexible wall would be desirable. However, by decreasing the thickness of the wall and by making it more flexible, it has been found that the chamber might collapse under a negative pressure condition and air might become aspirated to the patient.

It is, therefore, an object of the invention to provide a drip chamber that yields to priming easily but that will not callapse under a negative pressure condition, such as when restriction is added to the inlet port.

It is a further object of the present invention to provide a drip chamber that is relatively flexible but non-collapsible under a negative pressure condition, and that is simple in construction and easy to manufacture.

Other objects and advantages of the present invention will become apparent as the description proceeds.

BRIEF DESCRIPTION OF THE INVENTION

In accordance with the present invention, a drip chamber assembly is provided which comprises a flexible chamber formed of a vinyl plastic material having a thickness of about 0.04 inch to 0.08 inch and a durometer reading of about 61 shore A to 81 shore A.

In the illustrative embodiment, the drip chamber assembly includes a flexible plastic chamber, an inlet, a drop former, with the inlet communicating with the inside of the plastic chamber via the drop former. The chamber has a length of about 1.75 inches to 2.25 inches, an inside diameter of about 0.45 inch to 0.55 inch, and a volume of about 0.278 cubic inch to 0.535 cubic inch.

In the illustrative embodiment, end caps are provided to rigidly support each of the ends of the chamber. The end caps each have a contact length along the chamber of at least 0.2 inch. The end caps each comprise an inner circular member to which the chamber is bonded.

A more detailed explanation of the invention is provided in the following description and claims, and is illustrated in the accompanying drawings.

DETAILED DESCRIPTION OF THE ILLUSTRATIVE EMBODIMENT

Figure 1:
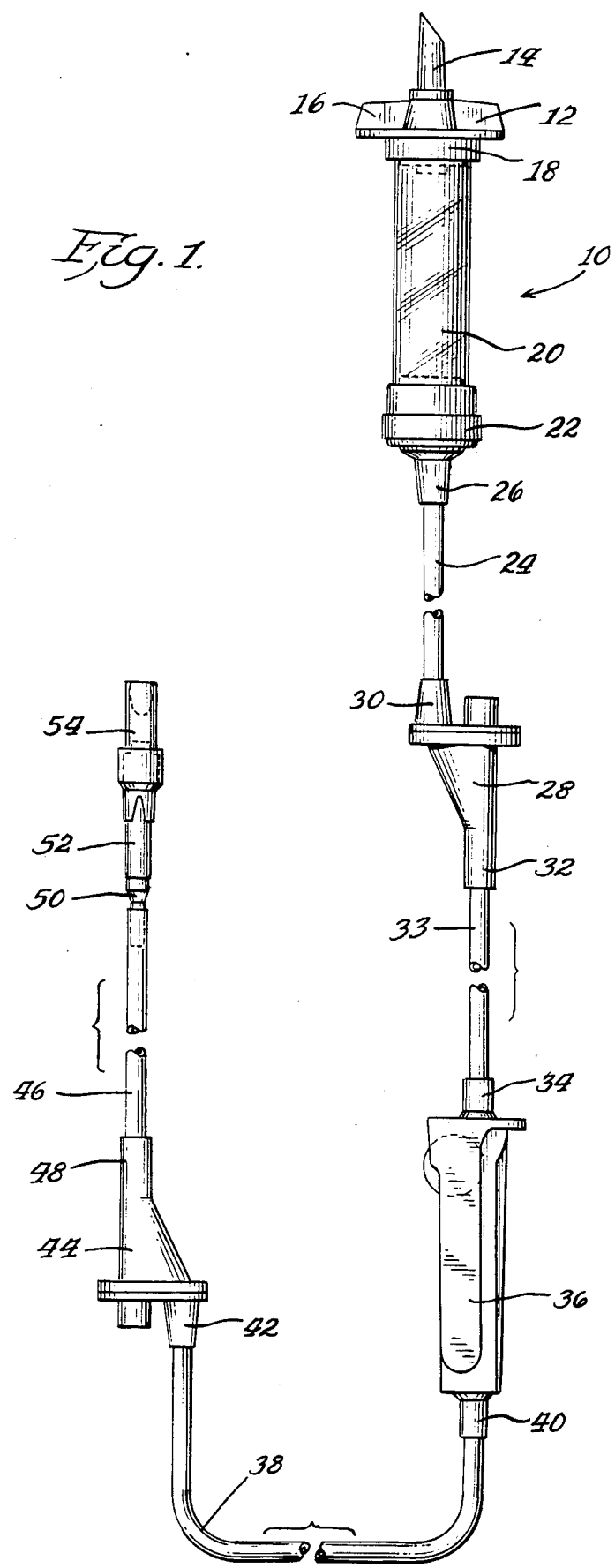
FIG. 1 is a view of an administration set with a drip chamber assembly constructed in accordance with the principles of the present invention.

The administration set illustrated in FIG. 1 includes drip chamber 10 having an inlet end cap 12 including inlet spike 14, wings 16 and end cap body portion 18, chamber 20, outlet or bottom end cap 22 enclosing a one-way check valve, tubing 24 connected to outlet 26, injection site 28 with inlet 30 thereof connected to tubing 24, tubing 33 connected to the outlet 32 of injection site 28 and the inlet 34 of a roller clamp 36, tubing 38 connected to the outlet 40 of roller clamp 36 and the inlet 42 of injection site 44, tubing 46 connected to the outlet 48 of injection site 44 and the inlet 50 of luer lock assembly 52, and a tip protector 54.

Spike 14 is intended for insertion into the outlet of a primary solution container. It is to be understood, however, that drip chamber 10 could be coupled to the outlet of a burette or to the outlet of any other type of liquid source.

Figure 2:
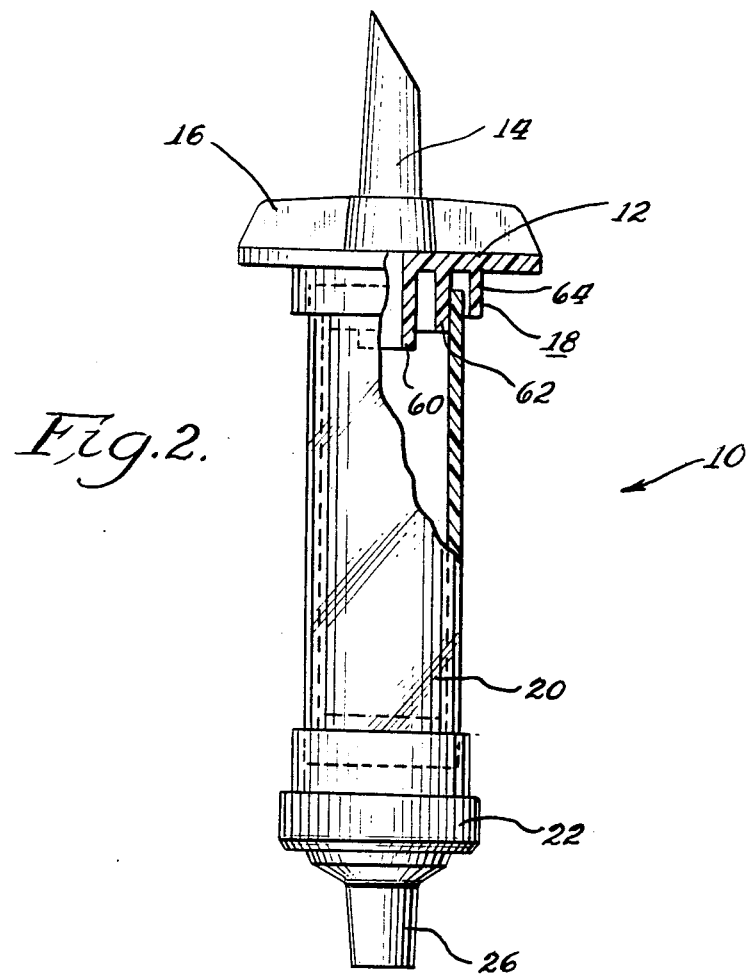
FIG. 2 is an elevational view of a drip chamber assembly constructed in accordance with the principles of the present invention.
Figure 3:
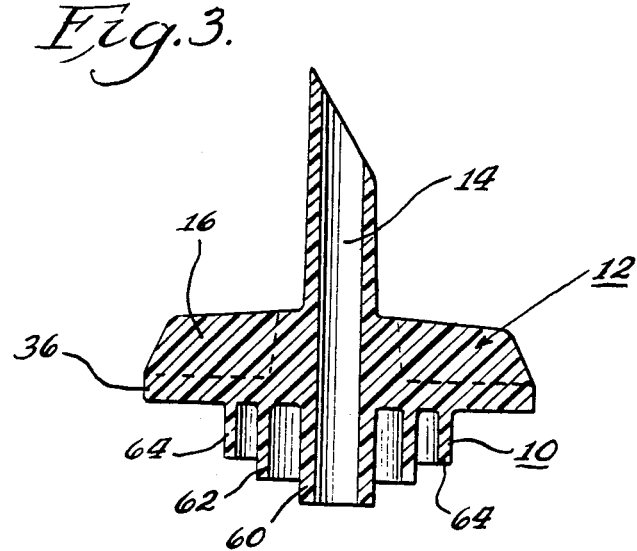
FIG. 3 is a cross-sectional elevation of the inlet end cap for the drip chamber assembly of FIG. 2.

The drip chamber assembly is shown in greater detail in FIGS. 2 and 3. Referring to these Figures, it can be seen that inlet end cap 12 effectively has three concentric circular members 60, 62 and 64, depending downwardly from a base portion 36. Member 60 comprises the drop former which defines a bore that is coaxial with the bore of spike 14. The inside of the vinyl plastic chamber is bonded to the outside of member 62. Member 64, which is spaced slightly from the plastic chamber, operates as a cover.

The vinyl plastic chamber has a length of between 1.75 inches to 2.25 inches, preferably 2.0 inches, an inside diameter of about 0.45 inch to 0.55 inch, preferably 0.50 inch. These dimensions result in a volume of about 0.278 cubic inch to 0.535 cubic inch. Chamber 20 is formed of a vinyl plastic material with a durometer reading of about 61 shore A to 81 shore A, with a thickness of about 0.04 inch to 0.08 inch.

Outlet end cap 22 has upwardly extending concentric members similar to members 62 and 64, for connection and cover, respectively of the vinyl plastic chamber 20. In addition, end cap 22 carries a one-way flex valve, preferably of the construction disclosed in Ruschke and Schwades U.S. patent application for "One-way Flex Valve", Ser. No. 942,076, filed Sept. 13, 1978 now U.S. Pat. No. 4,222,407.

The end caps rigidly support the opposed ends of the chamber 20 and have a contact length along the chamber of at least 0.2 inch, with the contact length preferably being between about 0.2 inch and 0.4 inch.

As a result of the aforementioned construction, the user may prime the chamber 20 one-half full with a single manipulation. The average user using his first two fingers and thumb would displace a volume of 0.139 cubic inch to 0.267 cubic inch with a single manipulation. The non-callapsing drip chamber will not collapse to a point of air aspiration with a vacuum pressure of 48 inches of water or 3.53 inches of mercury. The aforementioned parameters thus provide a non-collapsing drip chamber that is flexible enough to allow easy primary yet is non-collapsible under a negative pressure condition.

Although an illustrative embodiment of the invention has been shown and described, it is to be understood that various modifications and substitutions may be made by those skilled in the art without departing from the novel spirit and scope of the present invention.

What is claimed is:

1. A drip chamber assembly including a flexible plastic chamber, an inlet, a drop former, the inlet communicating with the inside of the plastic chamber via the drop former, the improvement comprising:

said chamber having a length of about 1.75 inches to 2.25 inches, a uniform inside diameter throughout its length of about 0.45 inch to 0.55 inch, and a volume of about 0.278 cubic inch to 0.535 cubic inch;

said chamber being formed of a vinyl plastic material with a durometer reading of about 61 shore A to 81 shore A;

said vinyl plastic material having a thickness of about 0.04 inch to 0.08 inch; and end caps rigidly supporting the ends of said chamber.

2. A drip chamber assembly as described in claim 1, said end caps each having a contact length along the chamber of at least 0.2 inch.

3. A drip chamber assembly as described in claim 2, said end caps each having a contact length along the chamber of about 0.2 inch to 0.4 inch.

4. A drip chamber assembly as described in claim 1, said end caps each comprising outer and inner circular members, said plastic chamber being bonded to said inner circular member.

5. A drip chamber assembly as described in claim 4, the bottom end cap carrying a one-way flex valve.

6. A drip chamber assembly including a flexible plastic chamber, an inlet, a drop former, the inlet communicating with the inside of the plastic chamber via the drop former, the improvement comprising:

said chamber being formed of a vinyl plastic material with a durometer reading of about 61 shore A to 81 shore A;

said chamber having a length of about 1.75 inches to 2.25 inches, a uniform inside diameter throughout its length of about 0.5 inch to 0.55 inch, and a volume of about 0.278 cubic inch to 0.535 cubic inch;

said vinyl plastic material having a thickness of about 0.04 inch to 0.08 inch; and a pair of end caps rigidly supporting the ends of said chamber, said end caps each having a contact length along the chamber of about 0.2 inch to 0.4 inch, said end caps comprising inner and outer circular members enclosing said chamber therebetween, and the bottom end cap carrying a one-way flex valve.

* * * * *